US012699703B2

(12) United States Patent
Yang et al.

(10) Patent No.: US 12,699,703 B2
(45) Date of Patent: Aug. 4, 2026

(54) GENERATIVE HIERARCHICAL SEARCHING FOR COMPOUNDS

(71) Applicant: GDM Holding LLC, Mountain View, CA (US)

(72) Inventors: Mengjiao Yang, Berkeley, CA (US); Simon Lutz Batzner, San Francisco, CA (US); Muratahan Aykol, San Jose, CA (US); Ruiqi Gao, San Francisco, CA (US); Alexander Lloyd Gaunt, Cambridgeshire (GB); Brendan Charles McMorrow, London (GB); Dale Eric Schuurmans, Edmonton (CA); Ekin Dogus Cubuk, Berkeley, CA (US); Igor Mordatch, Oakland, CA (US); Danilo Jimenez Rezende, London (GB)

(73) Assignee: GDM Holding LLC, Mountain View, CA (US)

( * ) Notice: Subject to any disclaimer, the term of this patent is extended or adjusted under 35 U.S.C. 154(b) by 0 days.

(21) Appl. No.: 19/484,186

(22) PCT Filed: May 21, 2025

(86) PCT No.: PCT/US2025/030389
§ 371 (c)(1),
(2) Date: Nov. 13, 2025

(87) PCT Pub. No.: WO2025/245236
PCT Pub. Date: Nov. 27, 2025

(65) Prior Publication Data
US 2026/0147775 A1     May 28, 2026

Related U.S. Application Data

(60) Provisional application No. 63/650,886, filed on May 22, 2024.

(51) Int. Cl.
*G16C 20/40* (2019.01)
*G06F 16/242* (2019.01)
(Continued)

(52) U.S. Cl.
CPC ...... *G06F 16/24578* (2019.01); *G06F 16/243* (2019.01); *G16C 20/40* (2019.02); *G16C 20/70* (2019.02)

(58) Field of Classification Search
CPC . G06F 16/24578; G06F 16/243; G16C 20/40; G16C 20/70
See application file for complete search history.

(56) References Cited

U.S. PATENT DOCUMENTS 5,495,604 A * 2/1996 Harding ............. G06F 16/2423
707/999.102
11,238,101 B1 * 2/2022 Mohajer .......... G06F 16/24575
(Continued)

OTHER PUBLICATIONS

Ajay et al., "Compositional foundation models for hierarchical planning." Advances in Neural Information Processing Systems 36, Dec. 2023, 22 pages.
(Continued)

*Primary Examiner* — Jorge A Casanova
(74) *Attorney, Agent, or Firm* — Fish & Richardson P.C.

(57) ABSTRACT

A method performed by one or more computers. The method comprises receiving a natural language query specifying requirements for a compound; processing the natural language query using a language policy to generate a plurality of representations of candidate compounds that each satisfy at least a subset of the requirements specified in the natural language query. Each representation specifies at least a chemical formula of the corresponding candidate compound. The method further comprises, for each representation in a subset of the representations, using a generative machine learning model conditioned on the representation to
(Continued)

generate one or more candidate chemical structures, each candidate chemical structure comprising a respective spatial location for each of the atoms of the corresponding candidate compound; and selecting a chemical structure and corresponding compound from the plurality of candidate chemical structures.

20 Claims, 5 Drawing Sheets

(51) Int. Cl.
    *G06F 16/2457*         (2019.01)
    *G16C 20/70*          (2019.01)

(56) References Cited

U.S. PATENT DOCUMENTS

| | | | | |
|---|---|---|---|---|
| 12,189,590 | B1 * | 1/2025 | Fan | G06F 16/243 |
| 2021/0057050 | A1 * | 2/2021 | Zavoronkovs | C07D 471/10 |
| 2021/0191936 | A1 * | 6/2021 | Khorasani | G06F 16/243 |
| 2021/0192131 | A1 * | 6/2021 | Levy | G06F 40/56 |
| 2022/0101276 | A1 * | 3/2022 | Banatao | G06Q 10/30 |
| 2023/0098398 | A1 * | 3/2023 | Xu | G16C 20/50 |
| | | | | 703/12 |
| 2023/0186025 | A1 * | 6/2023 | John | G06F 16/243 |
| | | | | 704/9 |
| 2024/0029836 | A1 * | 1/2024 | Nie | G16C 20/50 |
| 2024/0419835 | A1 * | 12/2024 | Karlberg | G06F 16/3329 |
| 2025/0166725 | A1 * | 5/2025 | Choi | G16B 15/30 |
| 2025/0189496 | A1 * | 6/2025 | Healey | G01N 30/8693 |
| 2025/0225108 | A1 * | 7/2025 | Sharma | G06F 16/212 |
| 2025/0225128 | A1 * | 7/2025 | Lazarev | G06F 16/243 |
| 2025/0225377 | A1 * | 7/2025 | Gabellini | G06F 16/338 |
| 2025/0232847 | A1 * | 7/2025 | Zavoronkovs | G16C 20/50 |
| 2025/0284888 | A1 * | 9/2025 | Khullar | G06F 40/205 |
| 2025/0321962 | A1 * | 10/2025 | Burger | G06F 16/24542 |
| 2025/0322916 | A1 * | 10/2025 | Chen | G06N 3/0455 |
| 2025/0328525 | A1 * | 10/2025 | Mishra | G06F 16/24522 |
| 2025/0328559 | A1 * | 10/2025 | Mey | G06N 3/0475 |
| 2025/0355897 | A1 * | 11/2025 | Sheetrit | G06F 16/285 |

OTHER PUBLICATIONS

Alayrac et al., "Flamingo: a Visual Language Model for Few-Shot Learning" CoRR, Submitted on Nov. 2022, arXiv:2204.14198v2, 54 pages.

Antunes et al., "Crystal structure generation with autoregressive large language modeling" CoRR, Submitted on Feb. 2024, arXiv:2307. 04340v3, 55 pages.

Blochl et al., "Projector augmented-wave method" Physical review B, Dec. 1994, 50(24): 17953-17979.

Çiçek et al., "3d u-net: learning dense volumetric segmentation from sparse annotation" CoRR, Submitted on Jun. 2016, arXiv:1606. 06650v1, 8 pages.

Court et al., "3-d inorganic crystal structure generation and property prediction via representation learning" Journal of Chemical Information and Modeling, Aug. 2020, 60(10): 4518-4535.

Cui et al., "A survey on multimodal large language models for autonomous driving" In Proceedings of the IEEE/CVF Winter Conference on Applications of Computer Vision, 2024, pp. 958-979.

Davies et al., "Smact: Semiconducting materials by analogy and chemical theory." Journal of Open Source Software 4.38, Jun. 2019, 1361: 3 pages.

Draxl et al., "The NOMAD laboratory: from data sharing to artificial intelligence." Journal of Physics: Materials 2.3, May 2019, 036001: 9 pages.

Du et al., "Learning universal policies via text-guided video generation." Advances in neural information processing systems 36, Dec. 2023, 17 pages.

Du et al., "Video language planning" CoRR, Submitted on Oct. 2023, arXiv:2310.10625v1, 17 pages.

Flam-Shepherd et al., "Language models can generate molecules, materials, and protein binding sites directly in three dimensions as XYZ, CIF, and PDB files" CoRR, Submitted on May 2023, arXiv:2305. 05708v1, 14 pages.

Google Gemini Team et al., "Gemini 1.5: Unlocking multimodal understanding across millions of tokens of context" CoRR, Submitted on Dec. 2024, arXiv:2403.05530v5, 154 pages.

Green et al., "The emergence of perovskite solar cells." Nature photonics 8.7, Jul. 2014, 506-514.

Gruver et al., "Fine-tuned language models generate stable inorganic materials as text" CoRR, Submitted on Jul. 2025, arXiv:2402. 04379v2, 20 pages.

Hellenbrandt, "The inorganic crystal structure database (ICSD)-present and future." Crystallography Reviews 10.1, Jan. 2004, 17-22.

Ho et al., "Cascaded diffusion models for high fidelity image generation." Journal of Machine Learning Research 23.47, 2022, 1-33.

Ho et al., "Imagen video: High definition video generation with diffusion models" CoRR, Submitted on Oct. 2022, arXiv:2210. 02303v1, 18 pages.

Ho et al., "Video diffusion models." Advances in neural information processing systems 35, Dec. 2022, 14 pages.

Hoffmann et al., "Data-Driven Approach to Encoding and Decoding 3-D Crystal Structures" CoRR, Submitted on Sep. 2019, arXiv:1909. 00949v1, 21 pages.

Holmes et al., "Evaluating large language models on a highly-specialized topic, radiation oncology physics." Frontiers in Oncology 13, Jul. 2023, 11 pages.

Ikebata et al., "Bayesian molecular design with a chemical language model." Journal of computer-aided molecular design 31.4, Apr. 2017, 379-391.

Jain et al., "Commentary: The Materials Project: A materials genome approach to accelerating materials innovation." APL materials 1.1, Jul. 2013, 011002: 1-11.

Kingma et al., "Adam: A Method for Stochastic Optimization" CoRR, Submitted on Jan. 2017, arXiv:1412.6980v9, 15 pages.

Kirklin et al., "The Open Quantum Materials Database (OQMD): assessing the accuracy of DFT formation energies." npj Computational Materials 1.1, Dec. 2015, 1-15.

Kresse et al., "Efficiency of ab-initio total energy calculations for metals and semiconductors using a plane-wave basis set." Computational materials science 6.1, Jul. 1996, 15-50.

Kresse et al., "Efficient iterative schemes for ab initio total-energy calculations using a plane-wave basis set." Physical review B 54.16, Oct. 1996, 11169-11186.

Kresse et al., "From ultrasoft pseudopotentials to the projector augmented-wave method." Physical review b 59.3, Jan. 1999, 1758-1774.

Lei et al., "Materials science in the era of large language models: a perspective" cond-mat, Submitted on Mar. 2024, arXiv:2403. 06949v1, 33 pages.

Liang et al., "Code as Policies: Language Model Programs for Embodied Control" CoRR, Submitted on May 2023, arXiv:2209. 07753v4, 16 pages.

Luu et al., "BioinspiredLLM: Conversational large language model for the mechanics of biological and bio-inspired materials." Advanced Science 11.10, Mar. 2024, 2306724: 1-16.

Mathew et al., "Atomate: A high-level interface to generate, execute, and analyze computational materials science workflows." Computational Materials Science 139, Nov. 2017, 22 pages.

Merchant et al., "Scaling deep learning for materials discovery." Nature 624.7990, Dec. 2023, 80-85.

Mizushima et al., "LixCoO2 (0<x<−1): A new cathode material for batteries of high energy density." Materials Research Bulletin 15.6, Jun. 1980, 783-789.

Momma et al., "VESTA 3 for three-dimensional visualization of crystal, volumetric and morphology data." Applied Crystallography 44.6, Dec. 2011, 1272-1276.

(56)         References Cited

OTHER PUBLICATIONS

Moret et al., "Leveraging molecular structure and bioactivity with chemical language models for de novo drug design." Nature Communications 14.1, Jan. 2023, 114: 12 pages.

Noh et al., "Inverse design of solid-state materials via a continuous representation." Matter 1.5, Nov. 2019, 1370-1384.

Ong et al., "Python Materials Genomics (pymatgen): A robust, open-source python library for materials analysis." Computational Materials Science 68, Feb. 2013, 314-319.

Openai.com [online], "Video generation models as world simulators" Feb. 2024, retrieved on Nov. 17, 2025, retrieved from URL <https://openai.com/index/video-generation-models-as-world-simulators/>, 50 pages.

Peebles et al., "Scalable diffusion models with transformers." Proceedings of the IEEE/CVF international conference on computer vision, 2023, 4195-4205.

Perdew et al., "Rationale for mixing exact exchange with density functional approximations." The Journal of chemical physics 105. 22, Dec. 1996, 9982-9985.

Ramesh et al., "Hierarchical Text-Conditional Image Generation with CLIP Latents" CoRR, Submitted on Apr. 2022, arXiv:2204. 06125v1, 27 pages.

Ramesh et al., "Zero-shot text-to-image generation" Paper, Presented at International conference on machine learning, Jul. 2021, 11 pages.

Rombach et al., "High-resolution image synthesis with latent diffusion models." Paper, Presented at Proceedings of the IEEE/CVF conference on computer vision and pattern recognition, 2022, 10684-10695.

Ronneberger et al., "U-Net: Convolutional Networks for Biomedical Image Segmentation" CoRR, Submitted on May 2015, arXiv:1505. 04597v1, 8 pages.

Saal et al., "Materials design and discovery with high-throughput density functional theory: the open quantum materials database (OQMD)." Jom 65.11, Nov. 2013, 1501-1509.

Saharia et al., "Photorealistic text-to-image diffusion models with deep language understanding." Advances in neural information processing systems 35, Dec. 2022, 16 pages.

Savinov et al., "Step-unrolled Denoising Autoencoders for Text Generation" CoRR, Submitted on Apr. 2022, arXiv:2112.06749v3, 23 pages.

Sun et al., "Scieval: A multi-level large language model evaluation benchmark for scientific research." Proceedings of the AAAI Conference on Artificial Intelligence. vol. 38. No. 17, Mar. 2024, 19053-19061.

Vahdat et al., "Score-based generative modeling in latent space." Advances in neural information processing systems 34, Dec. 2021, 16 pages.

Valmeekam et al., "Large language models still can't plan (a benchmark for llms on planning and reasoning about change)" CoRR, Submitted on Apr. 2023, arXiv:2206.10498v3, 21 pages.

Valmeekam et al., "On the planning abilities of large language models—a critical investigation." Advances in Neural Information Processing Systems 36, Dec. 2023, 13 pages.

Xie et al., "Translating natural language to planning goals with large-language models" CoRR, Submitted on Feb. 2023, arXiv:2302. 05128v1, 15 pages.

Xie et al., "Crystal diffusion variational autoencoder for periodic material generation" CoRR, Submitted on Mar. 2022, arXiv:2110. 06197v3, 20 pages.

Yang et al., "Learning interactive real-world simulators" CoRR, Submitted on Oct. 2023, arXiv:2310.06114v1, 26 pages.

Yang et al., "Scalable diffusion for materials generation" CoRR, Submitted on Jun. 2024, arXiv:2311.09235v2, 18 pages.

Zeni et al., "Mattergen: a generative model for inorganic materials design" CoRR, Submitted on Jan. 2024, arXiv:2312.03687v2, 56 pages.

Zhang et al., "Chemllm: A chemical large language model" CoRR, Submitted on Apr. 2042, arXiv:2402.06852v2, 26 pages.

Zhou et al., "Vision language models in autonomous driving and intelligent transportation systems" CoRR, Submitted on Oct. 2023, arXiv:2310.14414v1, 13 pages.

Bran et al., "Augmenting large language models with chemistry tools." Nature Machine Intelligence 6.5 (2024): 525-535.

Edwards et al., "Text2mol: Cross-modal molecule retrieval with natural language queries." Proceedings of the 2021 Conference on Empirical Methods in Natural Language Processing, Nov. 2021, 595-607.

Gong et al., "Text-Guided Molecule Generation with Diffusion Language Model" CoRR, Submitted on Feb. 2024, arXiv:2402. 13040v1, 9 pages.

International Search Report and Written Opinion in International Appln. No. PCT/US2025/030389, mailed on Sep. 26, 2025, 20 pages.

Invitation to Pay Additional Fees in International Appln. No. PCT/US2025/030389, mailed on Aug. 5, 2025, 16 pages.

Li et al., "Empowering Molecule Discovery for Molecule-Caption Translation with Large Language Models: A ChatGPT Perspective" CoRR, Submitted on Apr. 2024, arXiv:2306.06615v2, 13 pages.

Su et al., "A Molecular Multimodal Foundation Model Associating Molecule Graphs with Natural Language" CoRR, Submitted on Sep. 2022, arXiv:2209.05481v1, 17 pages.

Ye, "De novo drug design as GPT language modeling: large chemistry models with supervised and reinforcement learning." Journal of Computer-Aided Molecular Design 38.1, Dec. 2024, 20: 1-15.

Yirik et al., "MAYGEN: an open-source chemical structure generator for constitutional isomers based on the orderly generation principle." Journal of cheminformatics 13.1, Jul. 2021, 48: 1-14.

* cited by examiner

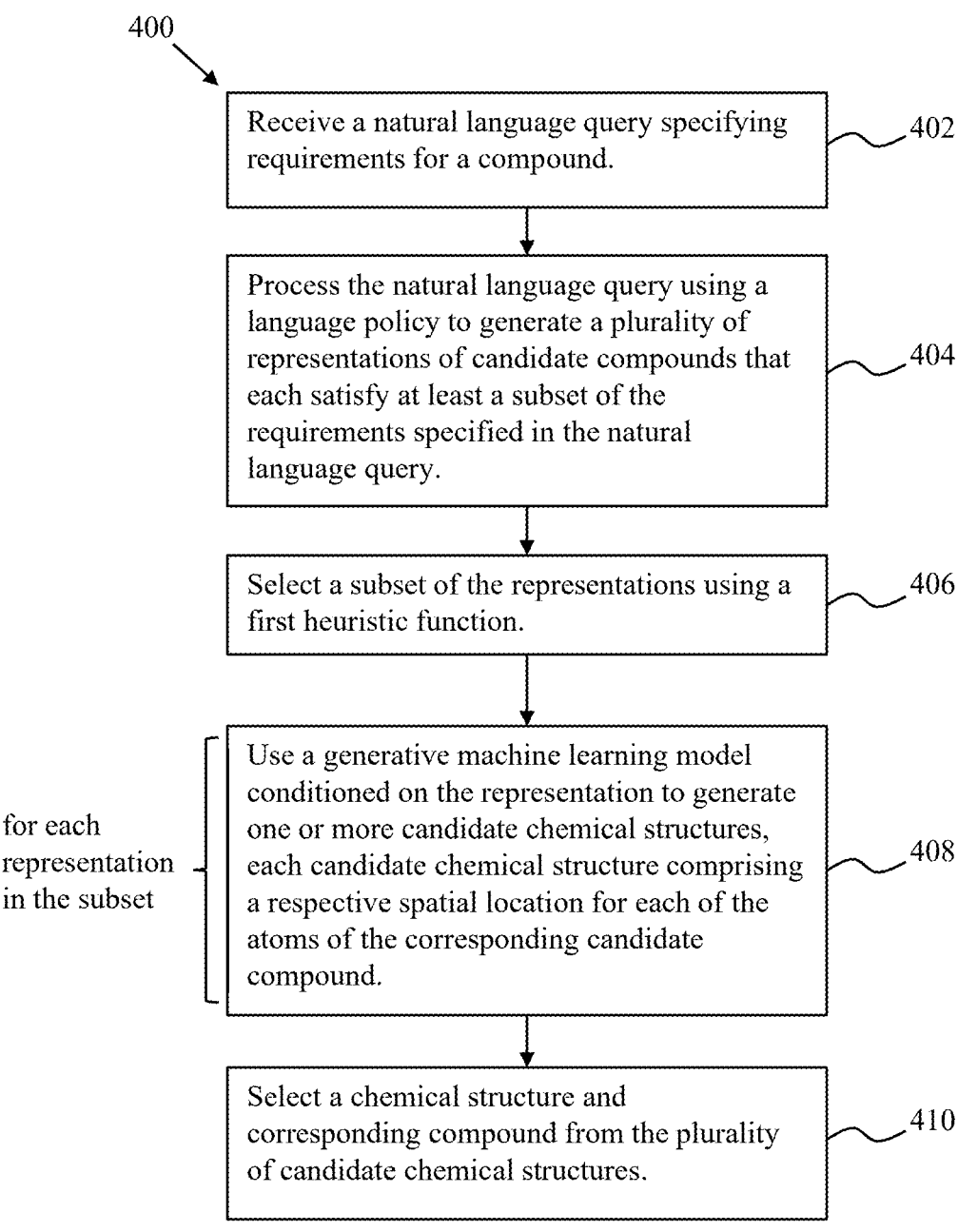

400

Receive a natural language query specifying requirements for a compound. — 402

Process the natural language query using a language policy to generate a plurality of representations of candidate compounds that each satisfy at least a subset of the requirements specified in the natural language query. — 404

Select a subset of the representations using a first heuristic function. — 406 for each representation in the subset

Use a generative machine learning model conditioned on the representation to generate one or more candidate chemical structures, each candidate chemical structure comprising a respective spatial location for each of the atoms of the corresponding candidate compound. — 408

Select a chemical structure and corresponding compound from the plurality of candidate chemical structures. — 410

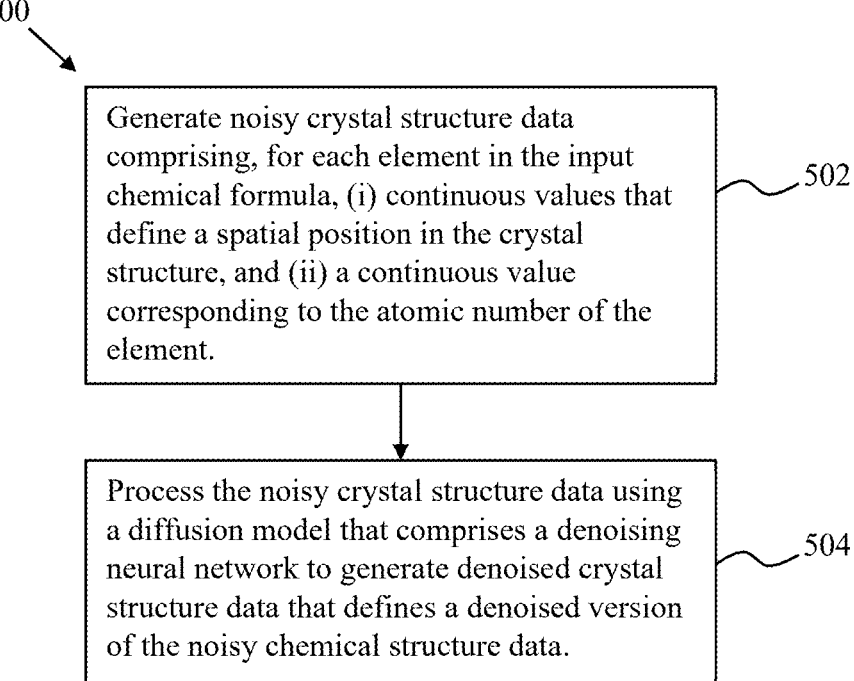

Generate noisy crystal structure data comprising, for each element in the input chemical formula, (i) continuous values that define a spatial position in the crystal structure, and (ii) a continuous value corresponding to the atomic number of the element.          502

Process the noisy crystal structure data using a diffusion model that comprises a denoising neural network to generate denoised crystal structure data that defines a denoised version of the noisy chemical structure data.          504

FIG. 5

GENERATIVE HIERARCHICAL SEARCHING FOR COMPOUNDS

CROSS-REFERENCE TO RELATED APPLICATION

This application is a National Stage Application under 35 U.S.C. § 371 and claims the benefit of International Application No. PCT/US2025/030389, filed May 21, 2025, which claims priority to U.S. Application No. 63/650,886, filed May 22, 2024, the disclosure of which is incorporated herein by reference.

BACKGROUND

This specification relates to processing data using machine learning models.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification generally describes systems and methods implemented as computer programs on one or more computers in one or more locations that can select a chemical compound based on a natural language query, e.g., provided by a user.

In one aspect there is provided a method performed by one or more computers. The method comprises: receiving a natural language query specifying requirements for a compound (i.e., a chemical compound, such as an inorganic compound, an organic molecule, a protein, a nucleic acid, a polysaccharide and so on) and then processing the natural language query using a language policy to generate a plurality of representations of candidate compounds that each satisfy at least a subset (e.g., one or more or all) of the requirements specified in the natural language query. Each representation may specify at least a chemical formula of the corresponding candidate compound. The method further comprises, for each representation in a subset of the representations (e.g., all of the representations, or a proper subset comprising one or more but not all of the representations), using a generative machine learning model conditioned on the representation to generate one or more candidate chemical structures. Each candidate chemical structure can comprise a respective spatial location for each of the atoms of the corresponding candidate compound (e.g., spatial locations in a unit cell of a crystal structure or spatial locations in a molecule, e.g., with respect to a centre of mass of the molecule); and selecting a chemical structure and corresponding compound from the plurality of candidate chemical structures.

The natural language query may be considered a "high-level" representation of a desired compound that is converted to lower-level "intermediate" representations of candidate compounds, which are then used to obtain "low-level" representations of the candidate compounds in the form of chemical structures. Thus, the method adopts a hierarchical approach to selecting a compound in response to the natural language query.

In some cases, the chemical formula may be a "reduced" chemical formula that specifies the relative numbers of each chemical element of the compound, when the compound might otherwise be more precisely represented by some multiple of the relative numbers of each chemical element. For example, the (reduced) chemical formula of a compound may be of the form $AB_2$, whereas the compound might be more precisely represented as $A_2B_4$ or $A_3B_6$., e.g., because the same chemical element may have different oxidation states in the compound. The generative machine learning model can then, for example, be capable of generating chemical structures corresponding to any combination of the chemical elements specified by the chemical formula, e.g., $AB_2$, $A_2B_4$, or $A_3B_6$, and so on. Thus, in some cases, the chemical formula of the compound can be updated by the generative machine learning model, e.g., such that the chemical formula of the chemical structure is different from the chemical formula that is specified in the corresponding representation of the compound.

In some implementations, the requirements may specify one or more chemical families (i.e., classes of chemical structures having one or more characteristics, such as stoichiometry, in common), e.g., a family of crystal structures, such as a Kagome lattice, a perovskite (e.g., double perovskite), a mxene, a pyrochlore, a spinel, and so on. As one example, the natural language query may comprise "Generate a stable novel chalcogenide with atom ratio 1:1:2". In some examples, the requirements may specify a particular motif (i.e., related to a particular biological function), e.g., a structure motif or a structural motif. An example of such a motif is a zinc finger motif, for a DNA-binding protein.

In some examples, the requirements may specify one or more of: a 2D or 3D structure, a particular physical property that the selected compound should have or exhibit (e.g., magnetism or superconductivity); a synthesis technique that can be used to synthesize the compound; one or more compounds to which the selected compound should be similar to or otherwise differ from; one or more pharmacological (e.g., pharmacokinetic and/or pharmacodynamic) properties of the compound; whether the compound should include radioactive atoms; and so on.

The requirements may specify a respective set of atomic numbers for one or more atoms in the compounds, e.g., by explicitly mentioning a chemical element (e.g., "the compound should contain iron or magnesium") or by specifying one or more of a group, row; or block of the periodic table (e.g., "the compound should be III-V semiconductor" or "the compound should contain a transition metal").

The language policy may comprise, for example, a (pre-trained) language model, such as an autoregressive language model, e.g., a large language model, LLM. The language model may, for example, generate the representations of the candidate compounds as text representations or multimodal representations that comprise text data (e.g., in addition to image data or data of one or more other modalities, such as amino acid sequence data), thereby providing at least some degree of human interpretability. In some cases, the language model may be optimized in some cases using techniques such as reinforcement learning from human feedback (RLHF). The language model can also allow the generation of the representations to be augmented using data obtained from sources (e.g., databases or repositories) other than the natural language query or the language model itself (so called retrieval augmented generation, RAG), e.g., by adding text information obtained from the internet and/or from one or more chemical, biochemical, protein structure or materials databases to the natural language query before it is processed by the language model.

In some implementations, the language model (language policy) may be prompted to generate representations of novel compounds by adding data about known compounds to the natural language query together with a requirement that the compound is not one of the known compounds.

In some implementations, the subset of the representations is selected using a first heuristic function that determines a respective likelihood that each of the representations satisfies the requirements specified in the natural language query. The first heuristic function may be a machine learning model configured to rank the representations according to the likelihood that each of the representations satisfies the requirements specified in the natural language query. The first heuristic function may, for example, comprise a pre-trained language model that may, for example, be prompted to rank the representations according to the likelihood that each of the representations satisfies the requirements specified in the natural language query. The language model may, for example, be trained (e.g., fine-tuned) using reinforcement learning from human feedback, for example. Generally speaking, a heuristic function may be a function that ranks alternatives according to some metric, and which can, for example, be used by a tree search algorithm to decide which branch or branches to follow.

In some implementations, determining the subset of the representations may comprise removing representations that do not meet one or more validity checks, e.g., a check whether the chemical formula can be parsed by a chemical formula parser (e.g., a regular expression parser), or a check that the compound is not one of a plurality of already known compounds.

In some implementations, the compound is an inorganic compound, and the candidate chemical structures are crystal structures. The inorganic compound may, for example, be an alloy. For example, the natural language query may comprise "Generate a novel steel with a melting point greater than 1300° C.".

In some implementations, the compound is a protein and the requirements identify one or more of secondary, tertiary and quaternary structure for the protein; and each of the chemical formulas defines a sequence of amino acids. For example, the natural language query may comprise "Generate a protein that includes alpha-helices and has a molecular weight of less than 60 kDa".

In some implementations, the compound is a ligand and the requirements identify a target molecule and/or binding site to which the ligand should bind. A "ligand" can refer to a molecule or other compound that is capable of binding to and forming a complex with a target molecule, e.g., a protein. Ligands can include, e.g., small organic compounds, macromolecules, and so forth. A ligand may associate or interact (e.g., through chemical bonds, or hydrogen bonds, or Van der Waals forces, or hydrophobic interaction, or electrostatic interaction, and so forth) to form a joint structure with the target molecule. In some implementations the ligand(s) may include small molecule complex ligands, e.g., organic compounds with a molecular weight of <900 daltons. In some other implementations the candidate ligand(s) may include polypeptide ligands, i.e., defined by an amino acid sequence.

For example, the ligand may be a drug or a ligand of an industrial enzyme; and selecting a chemical structure and corresponding compound from the plurality of candidate chemical structures comprises evaluating an interaction of each candidate chemical structure with the target molecule and/or binding site.

For example, the target molecule and/or binding site may comprise a receptor or enzyme, and wherein the selected ligand is an agonist or antagonist of the receptor or enzyme. As another example, the ligand may be a drug, and the requirements of the natural language query may identify a plurality of target molecules and/or binding sites; and selecting a chemical structure and corresponding compound from the plurality of candidate chemical structures comprises evaluating an interaction of each candidate chemical structure with each of the target molecules and/or binding sites to either (i) obtain a chemical structure that interacts with each of the target molecules and/or binding sites, or (ii) obtain a chemical structure that interacts with only one of the target molecules and/or binding sites.

In some implementations, the ligand is a polypeptide ligand, a polynucleoside ligand, or a polynucleotide ligand.

In some implementations, evaluating the interaction may include evaluating binding of the candidate ligand with the structure of the target molecule (such as a biological molecule). For example, evaluating the interaction may include identifying a ligand that binds with sufficient affinity for a biological effect. In some other implementations, evaluating the interaction may include evaluating an association of the candidate ligand with the target molecule which has an effect on a function of the target molecule, e.g., an enzyme. The evaluating may include evaluating an affinity between the candidate ligand and the target molecule or complex or evaluating a selectivity of the interaction. The candidate ligand(s) may be selected according to which have the highest affinity. Evaluating the interaction may additionally comprise simulating a dynamical behaviour of the ligand and target molecule, such as through molecular dynamics simulations, which may allow kinetic aspects of the interaction to be taken into account.

The evaluation of the interaction of a candidate ligand with the target molecule may be performed using a computer-aided approach in which graphical models of the candidate ligand and target molecule structure are displayed for user-manipulation, and/or the evaluation may be performed partially or completely automatically, for example using standard molecular (e.g., protein-ligand) docking software. In some implementations the evaluation may include determining an interaction score for the candidate ligand, where the interaction score includes a measure of an interaction between the candidate ligand and the target molecule. The interaction score may be dependent upon a strength and/or specificity of the interaction, e.g., a score dependent on binding free energy. A candidate ligand may be selected dependent upon its score.

In some implementations the target molecule includes a receptor or enzyme and the ligand is an agonist or antagonist of the receptor or enzyme. In some implementations the method may be used to identify the structure of a cell surface marker. This may then be used to identify a ligand, e.g., an antibody or aptamer or a label such as a fluorescent label, which binds to the cell surface marker. This may be used to identify and/or treat cancerous cells.

In some implementations the ligand is a drug and the interaction of each of a plurality of target molecules (such as a biological molecule) with each of the candidate ligands is evaluated. Then one or more of the candidate ligands may be selected either to obtain a ligand that (functionally) interacts with each of the target molecules, or to obtain a ligand that (functionally) interacts with only one of the target molecules. For example, in some implementations it may be desirable to obtain a drug that is effective against multiple drug targets. Also or instead, it may be desirable to screen a drug for off-target effects. For example, in agriculture it can be useful to determine that a drug designed for use with one plant species does not interact with another, different plant species and/or an animal species.

In some implementations the ligand is a drug and the target protein that is a protein complex, e.g., a dimer or multimer, is determined. Evaluating the interaction of the one or more candidate ligands with the target protein may then comprise identifying a candidate ligand that interacts with the protein complex, and that might therefore be expected to affect the formation or stability of the complex. This could afterwards be confirmed by experimental screening. Thus, such a process may be used to identify a drug which is able to disrupt a protein complex or inhibit formation of the complex. Some diseases, e.g., neuro degenerative diseases such as dementia, are caused by protein aggregation. The method may thus be used to identify a ligand that is a drug to treat such a disease.

In some implementations, the method further comprises synthesizing the ligand. The biological activity of the ligand may then be tested in vitro and/or in vivo. For example the ligand may be tested for ADME (absorption, distribution, metabolism, excretion) and/or toxicological properties, to screen out unsuitable ligands. The testing may include, e.g., bringing the candidate small molecule, polypeptide or polynucleotide ligand into contact with the target molecule (e.g., protein) and measuring a change in expression or activity of the target molecule.

In another aspect there is provided a method performed by one or more computers for determining a crystal structure of a compound defined by an input chemical formula. The method comprises: generating noisy crystal structure data comprising, for each atom (or element) in the input chemical formula, (i) continuous values (e.g., x, y, z coordinates) that define a spatial position in the crystal structure, and (ii) a continuous value corresponding to the atomic number ("atom number") of the element, wherein at least some (e.g., one or more or all) of the values in the noisy crystal structure data are sampled from a noise distribution; and processing the noisy crystal structure data using a diffusion model that comprises a denoising neural network to generate denoised crystal structure data that defines a denoised version of the noisy crystal structure data.

The denoised chemical structure data may, for example, define a respective final position and chemical element of each atom in the chemical structure. The atomic number can be represented by a "noisy" continuous value that can be denoised by the denoising neural network. Thus, the final chemical formula for the compound may differ from the input chemical formula, thereby allowing the method to generate more diverse crystal structures and/or allowing input formula to be a "reduced" chemical formula.

By representing the atomic number of each element as a continuous value, the noisy and denoised crystal structure data can be represented using a "dense" data structure which the denoising neural network can process with lower computational overhead than e.g., data structures where the atomic number is represented by a vector, such as a one-hot vector. For example, in some implementations, the noisy crystal structure and the denoised crystal structure data are $L{\times}4$ tensors, or $4{\times}L$ tensors, where L is the number of atoms (or elements) in the crystal structure. The continuous values for the atomic numbers may be normalized to a predetermined range such as −1 to 1, which may be the same as (or different from) a predetermined range to which the values defining the spatial positions (e.g., x, y, z coordinates) in the crystal structure are normalized.

In some implementations, the method further comprises: generating a respective crystal structure for each of a plurality of chemical formulas; and selecting the chemical structure and corresponding chemical formula from the plurality of crystal structures using a heuristic function based on respective predictions of one or more properties of each candidate chemical structure.

In some implementations, the method further comprises synthesizing the compound having the selected chemical formula. As examples, the synthesized compound may be used as a catalyst, e.g., in an industrial process, or it can be incorporated into one or more physical products (e.g., as a structural component), or it may be used to seed crystallisation of another compound or alloy, or it can be used in an optical component, such as a lens or a harmonic generation component (e.g., second-harmonic generation) crystal, and so on.

In some implementations, the compound is an inorganic compound, e.g., a mineral, ceramic, or an alloy. For example, the natural language query may comprise "Generate a novel steel with a melting point greater than $1300°$ C.".

A denoising (or "diffusion") neural network can refer to a neural network that, at any given time step, is configured to process a diffusion input that includes (i) a current noisy data item (noisy crystal structure data) and (ii) data specifying the given time step to generate a diffusion output that defines an estimate of a noise component of the current noisy data item given the current time step. The estimate of the noise component is an estimate of the noise that has been added to an original data item to generate the current noisy data item. After training, the trained denoising neural network is used to generate an output data item (denoised crystal structure data) across multiple time steps by performing a reverse diffusion process to gradually de-noise an initial data item until the final output data item is reached.

Some or all of the values in the initial data item are noisy values, i.e., are sampled from an appropriate noise distribution. That is, the initialized data item is the same dimensionality as the final data item but has noisy values. For example, the system can initialize the data item, i.e., can generate the first instance of the data item, by sampling each value in the data item from a corresponding noise distribution, e.g., a Gaussian distribution, a Normal distribution, or a different noise distribution. That is, the output data item includes multiple values and the initial data item includes the same number of values, with some or all of the values being sampled from a corresponding noise distribution. In some cases, all of the values in the initial data item are sampled from the noise distribution. In some other cases, some of the values are received as input by the system while others are sampled from the noise distribution. For example, the system may be using the diffusion neural network to complete, or otherwise modify an existing data item, and therefore certain values in the initial data item can be taken from the existing data item while the remainder are noisy values.

The subject matter described in this specification can be implemented in particular embodiments so as to realize one or more of the following advantages.

Generative models trained on large datasets can, in some cases, be used to generate novel chemical structures, such as crystal structures, molecular structures for organic or inorganic molecules, or protein structures. Compounds having these novel chemical structures can then be synthesized for use in a variety of applications and/or to confirm their physical properties. However, there are a number of challenges with developing generative models that are able to generate novel chemical structures that are, by definition, outside of the training data of the model, and which allow users, and in particular non-specialist users, to obtain appropriate outputs from the generative model, e.g., novel (or known) chemical structures that meet a given user's requirements. The latter issue can be addressed by allowing users to specify their requirements in natural language, but developing an end-to-end (natural) language-to-chemical structure generative model itself presents several challenges, including (i) a paucity of suitable training data, i.e., datasets that map natural language descriptions to chemical structures; (ii) the task of converting natural language to chemical structures is inherently multimodal as it requires converting discrete words into chemical structures defined by continuous values; and (iii) user descriptions of chemical structures may be vague as users may not know, or be able to articulate, all the relevant details of the types of chemical structures they are seeking.

The systems and methods described in the present disclosure address these issues by allowing users to specify their requirements in a natural language query, which is then used to identify a compound that meets these requirements (or at least a subset of them) using a two-stage approach comprising (a) a language-to-chemical formula(s) mapping; and (b) a chemical formula-to-chemical structure mapping. By dividing the task in two in this way, effective use can be made of (large) datasets that are already available, without the need to generate datasets for training an end-to-end language-to-chemical structure model.

In more detail, the natural language query is processed by a language policy (e.g., a language model) to generate representations of candidate compounds that satisfy at least a subset (i.e., one or more, or all) of the requirements specified in the natural language query. Each representation includes a chemical formula for the candidate chemical compound, which can then be used to predict a corresponding chemical structure for the compound. The representation can also include other information for generating the chemical structure, such as a point group for a molecule or a space group of a crystal structure. In the case where the compound is a protein, the chemical formula may be provided in the form of an amino acid sequence, for example. The language policy can be trained using, for example, the wealth of language-to-formula data available online, including Wikipedia articles, research papers, and textbooks.

A subset (i.e. one or more or all) of the representations generated by the language policy are then processed by a generative machine learning model (e.g., a diffusion model) to generate one or more candidate chemical structures for the candidate compound. For example, the generative machine learning model can generate multiple candidate chemical structures for the same input representation, e.g., to generate different isomers (e.g., stereoisomers) or crystal polymorphs, or, in some cases, to generate chemical structures/compounds that have a different chemical formula from the chemical formula specified in the representation. Thus, the generative machine learning model can be used to explore the space of chemical structures with the representation providing a starting point (or context) for the exploration. In general, the generative machine learning model can be trained using data obtained from one or more databases for chemical structures, such as protein structure repositories, materials databases, and crystallographic databases.

One or more of the chemical structures and corresponding compounds can be selected from the candidate chemical structures. The selection can be performed in many different ways, e.g., depending on the requirements specified in the natural language query. In one example, the selection may be performed based on a prediction of one or more properties of the candidate chemical structure, e.g., such as one or more physical properties, e.g., one or more of a formation energy (such as a free energy or enthalpy), a bandgap energy, a conductivity, or other electrical property (including e.g., superconductor properties, such as superconductor transition temperature); a magnetic property (e.g., permeability, Curie temperature); a mechanical property (e.g., bulk modulus, Young's modulus, density, ductility, strength, hardness); and a phase change property (e.g., a phase-change temperature, such as a melting or boiling point).

In some implementations, the selected chemical structure and corresponding compound may be selected from the plurality of candidate chemical structures using a second heuristic function (e.g., a "low-level" heuristic function), the selection being based on a prediction of one or more properties of each candidate chemical structure. The second heuristic function may comprise a machine learning model that has been trained to process an input comprising a chemical structure to generate an output comprising a prediction of one or more properties of the chemical structure.

The prediction of the one or more properties may be carried out by a trained machine learning model, such as a neural network. For example, the neural network may predict experimental properties of a chemical structure by leveraging available data of one or more similar chemical structures in a dataset of known materials on which the neural network has been trained. The neural network can have any appropriate neural network architecture. For example, the neural network can include any appropriate types of neural network layers (e.g., fully-connected layers, convolutional layers, attention layers, recurrent layers, etc.) in any appropriate numbers (e.g., 5 layers, 10 layers, or 100 layers) and connected in any appropriate configuration (e.g., as a linear sequence of layers or as a directed graph of layers). In some implementations, the neural network is a graph neural network (GNN), e.g., a GNN that has been trained to process an input comprising a chemical structure (e.g., a crystal structure or protein structure) to generate an output comprising an energy corresponding of the chemical structure (i.e., an "energy" GNN). The GNN may be trained using data augmentation in which partially relaxed (i.e., high energy) chemical structures are provided during training, e.g., by perturbing fully relaxed chemical structures present in the training data.

For example, the graph neural network may be configured to process a graph representation of a chemical (physical) structure of a material and to generate an embedding of the chemical structure. For example, the graph representation can represent atoms of the unit cell structure of a chemical structure with nodes having the respective atomic numbers of the atoms as node features. The graph representation can further include edges that connect the nodes representing atoms with inter-atom distances under a certain threshold. The edges can have the respective inter-atom distances as edge features. The graph neural network may process the embedding of the chemical structure to predict one or more properties of the chemical structure, e.g., properties that would be measured in a physical experiment if the chemical structure was synthesized.

Additionally or alternatively, the prediction of the one or more properties may be based, e.g., on electronic structure calculations, such as density functional theory (DFT) calculations, or on other types of calculations.

A search algorithm can be used to select the chemical structure and corresponding compound from the plurality of candidate compounds. For example, the representations for the candidate compounds and the corresponding candidate chemical (e.g., crystal) structures may define a tree data structure to which a tree search algorithm is applied to select one or more of the candidate chemical structures and corresponding candidate compounds. For example, the tree search algorithm may implement one of: a best-first search strategy; a breadth-first search strategy; and a depth-first search strategy. Alternatively, the search algorithm may be implemented in the form of a tree search neural network, which may improve the efficiency with which the space of possible compounds can be explored.

In some implementations, the language model (e.g., as part of the language policy and/or the first heuristic function) is a language model neural network (e.g., a language generation neural network). The natural language query can be tokenised to obtain an input token string that comprises text tokens, selected from a token vocabulary that represents words of a natural or computer language in which the natural language question is posed. The language model output can be configured to generate an output token string comprising one or more output tokens, i.e., text tokens selected from the token vocabulary, that defines a representation of a candidate compound The language model neural network may comprise a sequence-to-sequence model that receives an input string of natural or computer language text tokens and generates an output string of one or more natural or computer language text tokens, e.g., autoregressively, a token at a time. In general, any language model neural network may be used, e.g., an auto-regressive language generation neural network, or a language model neural network that does not rely on an auto-regressive model, such as a recurrent language model neural network or a denoising auto-encoder based language model (e.g., arXiv:2112.06749).

In some implementations, the language model neural network may be a multimodal language model neural network, e.g., one based on the "Flamingo" neural network described in "Flamingo: a Visual Language Model for Few-Shot Learning", Alayrac et al., arXiv:2204.14198.

It is surprising, but well-established, that large language models (language model neural networks) can perform tasks that they were not explicitly trained to perform. Thus, the language model may be used to generate representations of novel compounds.

The language model may have been trained using a scientific dataset, either during "pre-training" of the language model, or during "fine-tuning" of a language model that has been pre-trained using another dataset (which may be much larger than the scientific dataset).

Some implementations of the methods/systems described herein use large language model/language generation neural networks. Such a large language model may have greater than 1 billion, 10 billion or 100 billion trainable/trained parameters. It may have been trained on greater than 10 billion, 100 billion or 1000 billion words or tokens representing words.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 4 is a flow diagram of an exemplary process for selecting a compound based on a natural language query.

FIG. 5 is a flow diagram of an exemplary process for generating a crystal structure.

Like reference numbers and designations in the various drawings indicate like elements.

DETAILED DESCRIPTION

Figure 1:
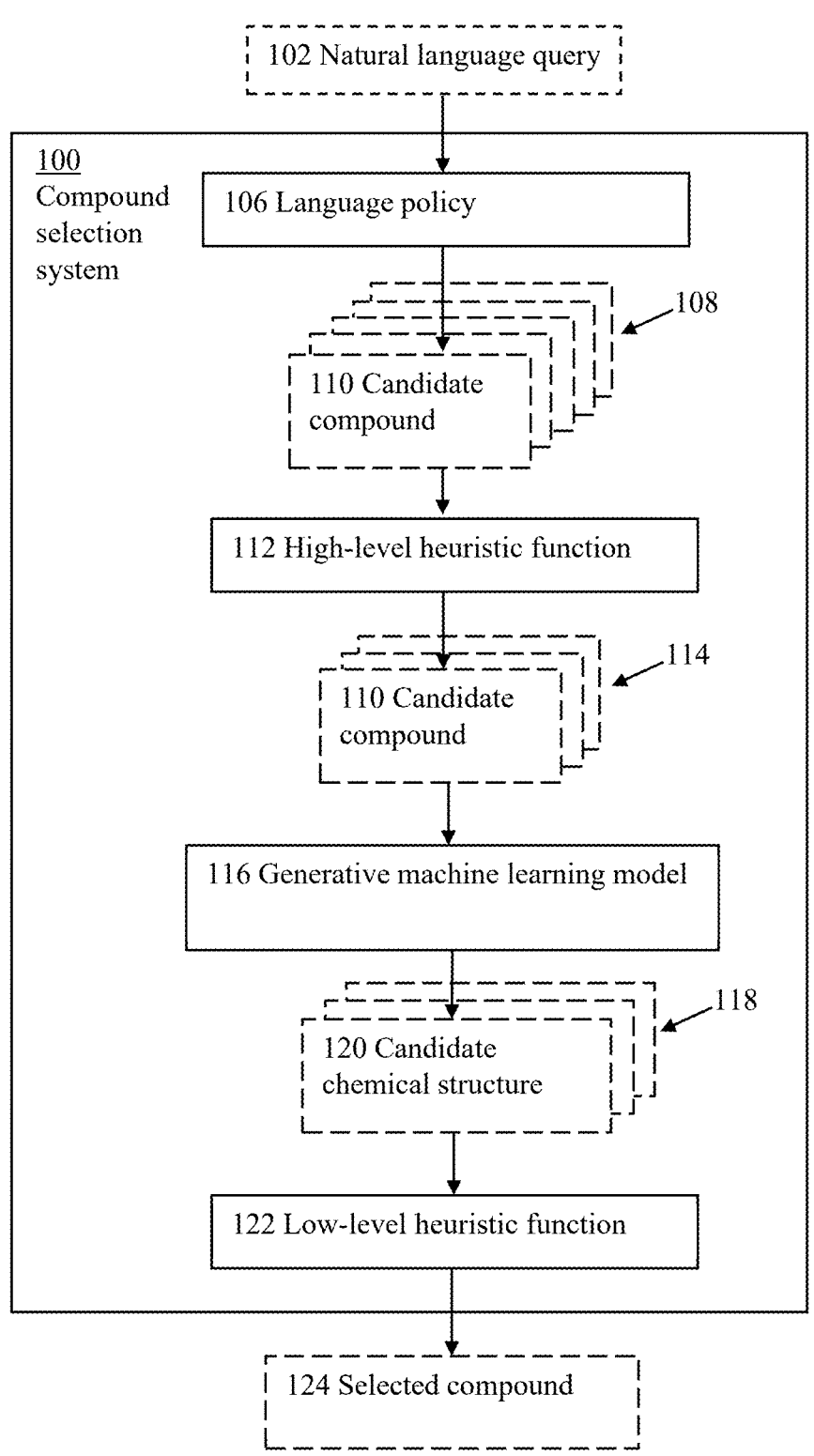
FIG. 1 shows an exemplary chemical compound selection system.

FIG. 1 shows an exemplary compound selection system 100. The compound selection system 100 is an example of a system implemented as computer programs on one or more computers in one or more locations in which the systems, components, and techniques described below are implemented.

The compound selection system 100 is configured to process a natural language query 102 specifying requirements for a chemical compound to generate a corresponding chemical compound 104.

The requirements in the natural language query 102 can comprise any appropriate requirement that characterizes compounds desired by the submitter of the natural language query 102. As one particular example, the natural language query may comprise "Generate a stable novel chalcogenide with atom ratio 1:1:2".

By way of further example, the requirements can specify one or more of: (i) one or more chemical families; (ii) particular elements that the compound should include; (iii) a 2D or 3D structure for the compound; (iv) a particular physical property that the selected compound should have or exhibit; (v) a particular motif (i.e., related to a particular biological function); (vi) a synthesis technique that can be used to synthesize the compound; (vii) one or more compounds to which the selected compound should be similar to or otherwise differ from; (viii) one or more pharmacological properties of the compound; (ix) whether the compound should include radioactive atoms; (x) a respective set of atomic numbers for one or more atoms in the compounds, e.g., by explicitly mentioning a chemical element (e.g., "the compound should contain iron or magnesium") or by specifying one or more of a group, row, or block of the periodic table (e.g., "the compound should be III-V semiconductor" or "the compound should contain a transition metal"); and so on.

The compound selection system 100 comprises a language policy 106 configured to process the natural language query 102 to generate a plurality of representations 108 of candidate compounds that each satisfy at least a subset of the requirements specified in the natural language query 102. In some implementations relating to crystalline compounds, each representation 110 specifies at least a chemical formula of the corresponding candidate compound. Each representation 110 can optionally additionally include information (e.g., text) identifying a space group of a crystal structure of the compound.

In the example shown in FIG. 1, the language policy 106 comprises a (pre-trained) language model, such as an autoregressive language model, e.g., a large language model, LLM, e.g., implemented as neural network. As one example, the language model 106 can comprise a multimodal model such as from the Gemini family of models, e.g., as described in Reid et al. "Gemini 1.5: Unlocking multimodal understanding across millions of tokens of context", arXiv: 2403.05530.

The representations generated by the language model can comprise text representations of the candidate compounds 110 or multimodal representations of the candidate compounds that comprise text data (e.g., in addition to image data or data of one or more other modalities, such as amino acid sequence data), thereby providing at least some degree of human interpretability. In some cases, the language model 106 may be optimized (fine-tuned) to generate suitable representations using techniques such as reinforcement learning from human feedback (RLHF).

In some implementations, the language model can be configured to augment the generation of the representations 110 using data obtained from sources (e.g., databases or repositories) other than the natural language query 102 or the language model itself, such as by so called retrieval augmented generation, RAG. For example, the language model 106 can add information (e.g., text information) obtained from the internet and/or from one or more chemical, biochemical, protein structure or materials databases to the natural language query 102 before it is processed by the language policy 106. As one particular example, the language policy 106 can comprise a deterministic retrieval function (not shown) that uses an application programming interface (API), such as the Wikipedia API, to retrieve textual information related to the natural language query 102, which is then processed by the language policy 106. The language policy 106 can be configured to then generate representations of the candidate compounds 110 conditioned on the retrieved textual information. For example, the language policy 106 can generate chemical formulae and space groups for the representations 110 conditioned on information retrieved from the internet or other source.

In some implementations, the language policy 106 can be prompted to generate representations of novel compounds by adding data about known compounds to the natural language query together with a requirement that the compound is not one of the known compounds. As one example, a prompt supplied to the language policy 106 can include chemical formula (and optionally, space group) for known compounds, e.g., every unique compound in one or more databases of compounds, together with an instruction that the generated compound should have a chemical formula (and optionally, space group) that is different from each of the known compounds.

The compound selection system 100 further comprises a high-level ("first") heuristic function 112 that is configured to select a subset 114 of the plurality of representations 108 for further processing by the compound selection system 100.

The high-level heuristic function 112 can be configured to remove representations 110 that do not meet one or more validity checks, e.g., a check whether the chemical formula can be parsed by a chemical formula parser (e.g., a regular expression parser), or a check that the compound is not one of a plurality of already known compounds, e.g., whether the compound appears in a database, such as the Materials Project database (https://next-gen.materialsproject.org/) or the Inorganic Crystal Structure Database (ICSD, https://www.psds.ac.uk/icsd), or a check that the chemical formula of the compound is compatible with the natural language query 102, e.g., by checking that there is an atom ratio of 113 for perovskites, 227 for pyrochlore, and 124 for spinel, and so on.

As one example, the high-level heuristic function 112 can be configured to determine a respective likelihood that each of the representations 110 satisfies the requirements specified in the natural language query 102. The subset 114 can then be determined by selecting representations 110 that having respective likelihoods exceeding a threshold likelihood or selecting the top-k representations according to the likelihoods, where k is a positive integer. Generally speaking, a high-level heuristic function (or the low-level heuristic function, see below) can be any function that ranks alternatives according to some metric, and which can, for example, be used by a tree search algorithm to decide which branch or branches to follow.

As one example, the high-level heuristic function 112 may be a machine learning model configured to rank the representations according to the likelihood that each of the representations satisfies the requirements specified in the natural language query 102. For example, the high-level heuristic function 112 may, for example, comprise a pre-trained language model, e.g., prompted to rank the representations 108 according to the likelihood that each of the representations 110 satisfies the requirements specified in the natural language query 102. The language model of the high-level heuristic function 112 may, for example, be trained (e.g., fine-tuned) using reinforcement learning from human feedback, for example.

The compound selection system 100 further comprises a generative machine learning model 114 configured to process the subset 114 of representations of candidate compounds to generate a plurality of candidate chemical structures 118. For each representation in the subset 114, the generative machine learning model is conditioned on the representation to generate a corresponding one or more candidate chemical structures 120. Each candidate chemical structure 120 comprises a respective spatial location for each of the atoms of the corresponding candidate compound. An example of the generative machine learning model 120 is further described below in connection with FIG. 3.

The compound selection system 100 further comprises a low-level ("second") heuristic function 122 configured to select one or more chemical structures and corresponding compounds from the plurality of candidate chemical structures 118. The low-level heuristic function 122 can, for example, make the selection based on a prediction of one or more properties of each candidate chemical structure.

For example, the low-level heuristic function 122 can comprise a machine learning model, such as a property prediction neural network, that has been trained to process an input comprising a chemical structure to generate an output comprising a prediction of one or more properties of the chemical structure.

For example, the property prediction neural network may predict experimental properties of a chemical structure by leveraging available data of one or more similar chemical structures in a dataset of known materials on which the property prediction neural network has been trained. The property prediction neural network can have any appropriate neural network architecture. For example, the property prediction neural network can include any appropriate types of neural network layers (e.g., fully-connected layers, convolutional layers, attention layers, recurrent layers, etc.) in any appropriate numbers (e.g., 5 layers, 10 layers, or 100 layers) and connected in any appropriate configuration (e.g., as a linear sequence of layers or as a directed graph of layers). In some implementations, the property prediction neural network is a graph neural network (GNN), e.g., a GNN that has been trained to process an input comprising a chemical structure (e.g., a crystal structure or protein structure) to generate an output comprising an energy corresponding of the chemical structure (i.e., an "energy" GNN). As one example, the GNN can be as described in Merchant et al. "Scaling deep learning for materials discovery", Nature, 624 (7990): 80-85, 2023.

In some cases, the GNN may be trained using data augmentation in which unrelaxed or partially relaxed (i.e., high energy) chemical structures are provided during training, e.g., by perturbing fully relaxed chemical structures present in the training data. This approach can mitigate the GNN learning to exploit irregularities in the predicted chemical structures. In some cases, any candidate chemical structures 120 predicted by the low-level heuristic function 122 to have energies outside a threshold range can be discarded.

For example, the graph neural network may be configured to process a graph representation of a chemical (physical) structure of a material and to generate an embedding of the chemical structure. For example, the graph representation can represent atoms of the unit cell structure of a chemical structure with nodes having the respective atomic numbers of the atoms as node features. The graph representation can further include edges that connect the nodes representing atoms with inter-atom distances under a certain threshold. The edges can have the respective inter-atom distances as edge features. The graph neural network may the process the embedding of the chemical structure to predict one or more properties of the chemical structure, e.g., properties that would be measured in a physical experiment if the chemical structure was synthesized. Additionally or alternatively, the prediction of the one or more properties may be based, e.g., on electronic structure calculations, such as density functional theory (DFT) calculations, or on other types of calculations. Standard ab initio simulation packages can be used for this purpose. As one example, the Vienna ab initio simulation package (VASP) with the Perdew-Burke-Ernzerhof (PBE) functional and projector-augmented wave (PAW) potentials can be used.

In some implementations, the low-level heuristic function 122 (e.g., property prediction neural network) can relax a candidate chemical structure prior to determining properties of the chemical structure, e.g., by performing a molecular dynamics simulation, or some other technique, such as simulated annealing.

The compound selection system 100 can implement a search algorithm to select a chemical structure and corresponding compound. For example, the representations for the candidate compounds and the corresponding candidate chemical structures may define a tree data structure to which a tree search algorithm is applied to select one or more of the candidate chemical structures and corresponding candidate compounds. For example, the tree data structure can comprise H high-level nodes that are each associated with a respective representation of a chemical compound, and each high-level node can have L low-level child nodes that are each associated with a candidate chemical structure for the chemical compound. The tree search algorithm can then determine which of the candidate chemical structures 120 and corresponding compound 110 best meets the requirements of the natural language query 102.

For example, the tree search algorithm may implement one of: a best-first search strategy; a breadth-first search strategy; and a depth-first search strategy. Alternatively, the search algorithm may be implemented in the form of a tree search neural network, which may improve the efficiency with which the space of possible compounds can be explored.

As one example of a best-first search algorithm that can be performed by the compound selection system 100, the system can generate, based on the natural language query 102, a plurality of representations 108 of candidate compounds that each comprises a respective chemical formula, and then use the high-level heuristic function 112 to prune and rank the chemical formulae. For example, high-level heuristic function 112 can check that the chemical formulae are valid (e.g., using a regular expression checker), and new (e.g., not found in an existing database of compounds), and compatible with the natural language query 102, e.g., has a correct stoichiometry. The high-level heuristic function 112 can then rank chemical formulae that pass these checks, e.g., by using a pre-trained (large) language model to rank the chemical formulae by how likely they are to are to meet the requirements of the natural language query 102 (e.g., a user request). The system 100 can then select a pre-determined number of the top-ranked chemical formulae for processing by the generative machine learning model 116, which then generates a plurality of candidate chemical structures 118 for each of the candidate chemical formulae. The low-level heuristic function 122 is then used to rank the candidate chemical structures 118 and the top-ranking chemical structure for each of the chemical formulae selected. The selected compound 124 can then be selected from the top-ranking chemical structures of the chemical formulae, e.g., by ranking the chemical structures using the low-level heuristic function 122, e.g., based on the formation energy of each chemical structure.

The choice of search algorithm can, for example, depend on the choice of low-level heuristic function 122 and the available computational resources. For example, if large-scale density functional theory (DFT) calculations are available as part of use by the low-level heuristic function 122 then a breadth-first search can be used so that more diverse compounds are considered.

In mathematical terms, the compound selection system 100 is configured to solve an optimization problem of the form:

$$z^*, x^* = \arg\max_{z, x \sim \pi_{hi}, \pi_{lo}} \mathbb{E}_{z \sim \pi_{hi}, x \sim \pi_{lo}(z)}[\lambda_{hi} \cdot R_{hi}(g, z) + \lambda_{lo} \cdot R_{lo}(z, x)]$$

In which: $z^*$ is the optimum chemical compound (e.g., chemical formula, and optionally, for crystalline compounds, space group), $x^*$ is the optimum structure for the chemical compound, which together with $z^*$ jointly optimizes the objective on the right-hand side of the equation; $\pi_{hi}$ is the language policy 106 that maps a natural language query g to a distribution from which representations of candidate compounds z can be sampled; $\pi_{lo}(z)$ is the generative machine learning model 116 (e.g., denoising neural network) that maps a representation 110 of a candidate compound z to a distribution from which candidate chemical structures x can be sampled; $R_{hi}(g, z)$ is the high-level heuristic function 112 mapping the natural language query 102 and representation 110 of a candidate compound to a score; $R_{lo}(z, x)$ is the low-level heuristic function 122 that maps the representation of a candidate compound and a candidate chemical structure for the compound to a score; and $\lambda_{hi}$ and $\lambda_{lo}$ are hyperparameters to control how much weight to put on the high-level and low-level heuristic functions. In general, $R_{hi}$ and $R_{lo}$ can each be combinations of multiple objectives. For example, $R_{lo}$ can be a weighted sum of properties of the candidate chemical structure, such as bandgap, conductivity, and formation energy.

Figure 2:
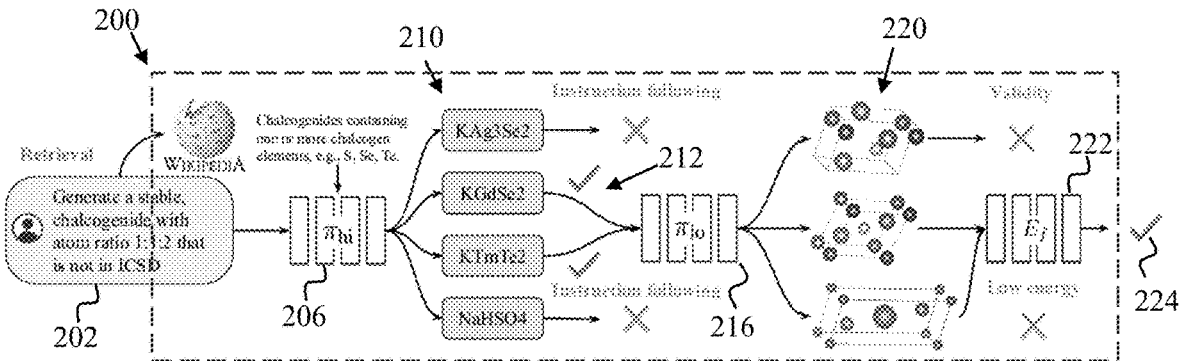
FIG. 2 is a schematic view of a particular implementation of the chemical compound selection system of FIG. 1 being used to select a chemical compound.

FIG. 2 shows schematically the processing of a natural language query 202 comprising the text "Generate a stable, chalcogenide with atom ratio 1:1:2 that is not in ICSD" by a particular implementation 200 of the compound selection system 100 of FIG. 1. In this example, the language policy 206 uses the natural language query 202 to obtain information about chalcogenides using the Wikipedia API. In this example, the retrieved information comprises "Chalcogenides containing one or more chalcogen elements, e.g., S, Se, Te". The language policy 206 then uses this information and the natural language query 202 to determine respective text representations of a plurality of candidate compounds 210, in this example "$KAg_3Se_2$", "$KGdSe_2$", "$KTmTe_2$", "$NaHSO_4$".

The compound selection system 200 then selects a subset 212 of the candidate compounds 210 using a high-level heuristic function (not shown), which determines whether each of the candidate compounds is compatible with the natural language query 202. In the present example, $KGdSe_2$ and $KTmTe_2$ are selected as being compatible. The compound selection system 200 then uses the generative machine learning model 216 to generate chemical structures 220 for each of the selected candidate compounds 212.

The low-level heuristic function 222 in this example is a graph neural network that is configured to rank the chemical structures 220 according to their predicted formation energy. In this example, the low-level heuristic function 222 also comprises additional checkers that assess structural and compositional validity of the chemical structures. Examples of such checkers are described in, for example, Xie et al. "Crystal diffusion variational autoencoder for periodic material generation" arXiv:2110.06197.

The compound 224 having the highest-ranking chemical structure is then selected for output by the system 200.

Figure 3:
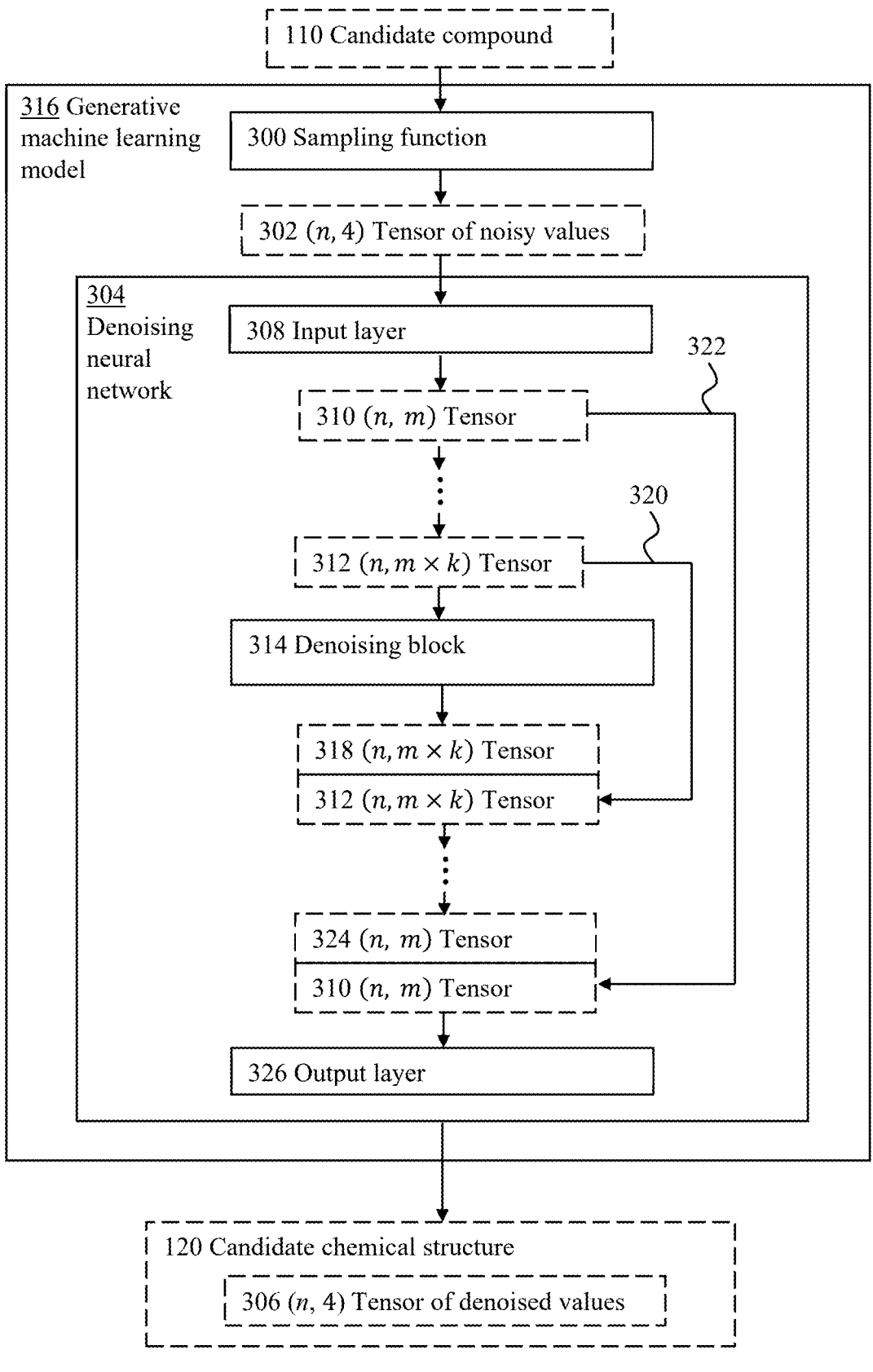
FIG. 3 shows an exemplary generative machine learning model for generating chemical structures.

FIG. 3 shows an example generative machine learning model 316 that can be used as the generative machine learning model 116 described above in connection with FIG. 1. The generative machine learning model 316 is an example of a system implemented as computer programs on one or more computers in one or more locations in which the systems, components, and techniques described below are implemented.

The generative machine learning model 316 is configured to process a representation 110 of a candidate compound and generate one or more candidate chemical structures 120 based on the representation 110. In the present example, the candidate chemical structures 120 generated by the generative machine learning model 316 are crystal structures, but the generative machine learning model 316 can be configured to generate other types of chemical structure, such as molecular structures and protein structures, instead of or as well as crystal structures.

The generative machine learning model 316 comprises a sampling function 300 configured to process the representation 110 of the candidate compound and generate noisy crystal structure data comprising, for each atom in the chemical formula, (i) continuous values that define a spatial position in the crystal structure, e.g., x, y, z coordinates, and (ii) a continuous value corresponding to the atomic number of the atom. The sampling function is used to sample at least some of the values from a respective noise distribution, e.g., a Gaussian noise distribution. The noisy crystal structure data 302 are arranged in the present example as an (n, 4) tensor of noisy values, where n is the number of atoms (e.g., elements) in the chemical formula. Directly representing the atomic number of each atom as a continuous value can improve inference speed, as opposed to e.g., representing the atomic number using a one-hot vector. The noisy crystal structure data can additionally comprise other data (not shown) to define the lattice structure of the crystal structure, e.g., angles and lengths of the unit cell of the crystal structure (which can be represented as two 3-vectors), for example.

The generative machine learning model 316 comprises a denoising neural network ("diffusion model") 304 configured to process the noisy crystal structure data 302 and generate corresponding denoised crystal structure data defining a denoised version 306 of the noisy crystal structure data, which in this example is arranged as an (n, 4) tensor of denoised values. The continuous values corresponding to the atomic numbers of the atom can be normalized to the range of input values of the denoising neural network 304.

The denoising neural network 304 generates the denoised crystal structure data across multiple "time" steps by performing a reverse diffusion process to gradually de-noise the noisy crystal structure data until the final denoised crystal structure data 306 is obtained.

The denoising neural network 304 comprises an input layer 308, e.g., a multi-layer perceptron (MLP), that processes the (n, 4) tensor of noisy values and generates an (n, m) tensor 310 comprising, for each of the n atoms, a representation of size m (e.g., an integer greater than four, e.g., 256).

The denoising neural network 304 can further comprise a plurality of denoising blocks 314 that increase the size of the tensor further, e.g., by increasing the size of the representation by the same amount, e.g., such that after k−1 denoising blocks, the (n, m) tensor 310 has been expanded to an (n, m×k) tensor 312. Optionally, the final denoising block can maintain the size of the tensor. Each denoising block 314 can, for example, comprise a multi-layer perceptron (MLP), followed by a self-attention layer, e.g., an order invariant self-attention layer, that applies a self-attention mechanism over the atoms. The self-attention mechanism can comprise a multi-headed self-attention mechanism, for example.

The denoising neural network 304 has a U-Net-style architecture that makes use of the concatenation of skip connections during the denoising of the noisy crystal structure data. For example, the denoising neural network 304 comprises a skip connection 320 that concatenates the (n, m×k) tensor 318 generated by the final denoising block 314 with the (n, m×k) tensor 313 provided as input to the denoising block 314.

The denoising neural network 304 comprises further layers (not shown), such as MLPs, that are configured to reduce the size of the (n, m×k) tensor 318 generated by the final denoising block after concatenation with the (n, m×k) tensor 313 provided as input to the denoising block 314. The denoising neural network 304 can be configured such that each of the further layers decreases the size of the tensor so that the resulting tensor 324 can be concatenated with an earlier tensor 310 of the same dimension by a corresponding skip connection 322.

The denoising neural network 304 further comprises an output layer 326 (e.g., an MLP) configured to process the final tensor formed by concatenating the last (n, m) tensor 324 with the first (n, m) tensor 310 to generate the tensor of denoised values 306, which defines the candidate chemical structure 120.

The denoising neural network 304 can be trained using training data comprising training examples that each comprise a training input comprising a representation of a compound 110 (e.g., a chemical formula for the compound) and a target output comprising a chemical structure 120 for the compound. Parameters of the denoising neural network 304 can then be adjusted to optimize an objective function that compares predicted chemical structures 120 generated by the denoising neural network 304 based on the representations of the compounds in the training inputs with the corresponding training outputs. The objective function can, for example, measure errors (e.g., mean squared errors) between the 3D positions of the atoms in the predicted and target chemical structures for each of the chemical compounds in the training inputs of the training examples. Standard training methods for training denoising neural networks can be used, e.g., based on backpropagation of gradients with respect to the parameters of the denoising neural network 304 of the objective function through the denoising neural network. As one example, the Adam optimizer can be used to perform the optimization, see e.g., Kingma et al., arXiv:1412.6980.

By way of a particular example, the following hyperparameter values and options can be used for training the denoising neural network 100: Learning rate, 5e-5; Optimizer, Adam ($\beta_1$=0.9, $\beta_2$=0.99), Base hidden dimension, 256; Hidden dimension multipliers 1, 2, 4; Number of denoising blocks, 9; Batch size 512; Exponential Moving Average (EMA), 0.9999; Weight decay 0.0; Prediction target, $\epsilon$; Attention head dimension, 64; Dropout, 0.1; Training hardware, 64 TPU-v4 chips; Diffusion noise schedule cosine; Noise schedule log SNR range, [−20, 20]; Training steps 200,000; Sampling timesteps, 256; Sampling logvariance interpolation, $\gamma$=0.1.

FIG. 4 is a flow diagram of an example process 400 for selecting a chemical compound based on a natural language query. For convenience, the process 400 will be described as being performed by a system of one or more computers located in one or more locations. For example, a chemical compound selection system, such as the chemical compound selection system 100 of FIG. 1, appropriately programmed in accordance with this specification can perform the process 400.

The system receives 402 a natural language query specifying requirements for a compound and then processes 404 the natural language query using a language policy to generate a plurality of representations of candidate compounds that each satisfy at least a subset of the requirements specified in the natural language query.

The system selects 406 a subset of the representations using a first heuristic function. For each representation in the subset, the system uses 408 a generative machine learning model conditioned on the representation to generate one or more candidate chemical structures. Each candidate chemical structure comprises a respective spatial location for each of the atoms of the corresponding candidate compound.

The system then selects 410 a chemical structure and corresponding compound from the plurality of candidate chemical structures.

FIG. 5 shows a flow diagram of an example process 500 for generating a crystal structure. For convenience, the process 500 will be described as being performed by a system of one or more computers located in one or more locations. For example, a generative machine learning model, such as the generative machine learning model 316 of FIG. 3, appropriately programmed in accordance with this specification can perform the process 500.

The system generates 502 noisy crystal structure data comprising, for each element in an input chemical formula, (i) continuous values that define a spatial position in the crystal structure, and (ii) a continuous value corresponding to the atomic number of the element. The system then processes 504 the noisy crystal structure data using a diffusion model that comprises a denoising neural network to generate denoised crystal structure data that defines a denoised version of the noisy chemical structure data.

The system and methods described in this specification have been found to significantly outperform LLM prompting baselines in producing unique and low-energy (as predicted by a GNN) structures that satisfy user requests. For example, the hierarchical approach described herein has been found to outperform multi-shot prompted LLMs for different families of chemical structures, such as perovskites, pyrochlores, and spinels, over a range of metrics, such as formation energy, composition validity, uniqueness, structural validity, compositional validity, and so on.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them. Thus a system, artificial neural network, or trained artificial neural network as described herein, can be implemented in hardware using electronic circuitry, e.g., in a physical box. Similarly computer code as described herein can be code to emulate such hardware or code for a hardware description language.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a standalone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A method performed by one or more computers, the method comprising:

receiving a natural language query specifying requirements for a compound;

processing the natural language query using a language policy to generate a plurality of representations of candidate compounds that each satisfy at least a subset of the requirements specified in the natural language query, each representation specifying at least a chemical formula of the corresponding candidate compound;

for each representation in a subset of the representations, using a generative machine learning model conditioned on the representation to generate one or more candidate chemical structures, each candidate chemical structure comprising a respective spatial location for each of the atoms of the corresponding candidate compound; and selecting a chemical structure and corresponding compound from the plurality of candidate chemical structures.

2. The method of claim 1, wherein the subset of the representations is selected using a first heuristic function that determines a respective likelihood that each of the representations satisfies the requirements specified in the natural language query.

3. The method of claim 2, wherein the first heuristic function comprises a pre-trained language model.

4. The method of claim 3, wherein the pre-trained language model is prompted to rank the representations according to the respective likelihood that each of the representations satisfies the requirements specified in the natural language query.

5. The method of claim 1, wherein the selected chemical structure and corresponding compound is selected from the plurality of candidate chemical structures using a second heuristic function, the selection being based on a prediction of one or more properties of each candidate chemical structure.

6. The method of claim 5, wherein the second heuristic function comprises a machine learning model that has been trained to process an input comprising a chemical structure to generate an output comprising a prediction of one or more properties of the chemical structure.

7. The method of claim 6, wherein the one or more properties of the chemical structure comprise one or more of: a formation energy; a bandgap energy; a conductivity; a magnetic property; an electrical property; a mechanical property; and a phase change property.

8. The method of claim 7, wherein the machine learning model is a graph neural network.

9. The method of claim 1, wherein selecting the chemical structure and corresponding compound from the plurality of candidate chemical structures comprises performing a tree search over the representations and candidate chemical structures.

10. The method of claim 9, wherein the tree search uses one of: a best-first search strategy; a breadth-first search strategy; and a depth-first search strategy.

11. The method of claim 1, wherein the language policy comprises a language model that processes the natural language query to generate the plurality of representations of candidate compounds.

12. The method of claim 11, wherein the language policy comprises a retrieval policy that processes the natural language query to retrieve data relating to the natural language query from one or more repositories, and wherein the language model is conditioned on the data retrieved from the one or more repositories.

13. The method of claim 12, wherein the data retrieved from the one or more repositories is added to the natural language query before the language model processes the natural language query.

14. The method of claim 1, wherein each representation identifies a point group or space group for the corresponding candidate chemical structure.

15. The method of claim 1, wherein each representation is a text representation or a multimodal representation that comprises text data.

16. The method of claim 1, wherein the natural language query comprises a plurality of known chemical formulas and the requirements specify that the compound is not one of the plurality of known chemical formulas.

17. The method of claim 1, wherein the requirements specify a chemical family for the compound.

18. The method of claim 1, wherein the requirements specify a stoichiometry or range of stoichiometries for the compound.

19. One or more non-transitory computer storage media storing instructions that when executed by one or more computers cause the one or more computers to perform operations comprising:

receiving a natural language query specifying requirements for a compound;

processing the natural language query using a language policy to generate a plurality of representations of candidate compounds that each satisfy at least a subset of the requirements specified in the natural language query, each representation specifying at least a chemical formula of the corresponding candidate compound;

for each representation in a subset of the representations, using a generative machine learning model conditioned on the representation to generate one or more candidate chemical structures, each candidate chemical structure comprising a respective spatial location for each of the atoms of the corresponding candidate compound; and selecting a chemical structure and corresponding compound from the plurality of candidate chemical structures.

20. A system comprising:

one or more computers; and one or more storage devices communicatively coupled to the one or more computers, wherein the one or more storage devices store instructions that, when executed by the one or more computers, cause the one or more computers to perform operations comprising:

receiving a natural language query specifying requirements for a compound;

processing the natural language query using a language policy to generate a plurality of representations of candidate compounds that each satisfy at least a subset of the requirements specified in the natural language query, each representation specifying at least a chemical formula of the corresponding candidate compound;

for each representation in a subset of the representations, using a generative machine learning model conditioned on the representation to generate one or more candidate chemical structures, each candidate chemical structure comprising a respective spatial location for each of the atoms of the corresponding candidate compound; and selecting a chemical structure and corresponding compound from the plurality of candidate chemical structures.

* * * * *